United States Patent [19]

Sonoyama et al.

[11] Patent Number: 4,748,122
[45] Date of Patent: May 31, 1988

[54] 2,5-DIKETO-D-GLUCONIC ACID REDUCTASE

[75] Inventors: Takayasu Sonoyama; Bunji Kageyama; Kobee Kobayashi, all of Osaka; Masahiro Tanimoto, Hyogo, all of Japan

[73] Assignee: Shionogi & Co., Ltd., Osaka, Japan

[21] Appl. No.: 665,965

[22] Filed: Oct. 29, 1984

[30] Foreign Application Priority Data

Nov. 17, 1983 [JP] Japan ................. 58-217176

[51] Int. Cl.$^4$ ............... C12N 9/02; C12P 19/02; C12P 7/60; C12R 1/15
[52] U.S. Cl. .................. 435/189; 435/105; 435/138; 435/843
[58] Field of Search .............. 435/189, 138, 105

[56] References Cited

U.S. PATENT DOCUMENTS 3,922,194  11/1975  Sonoyama et al. .............. 435/138
3,959,076   5/1976  Sonoyama et al. .............. 435/138
3,963,574   6/1976  Sonoyama et al. .............. 435/138
3,998,697  12/1976  Sonoyama et al. ............ 435/138 X

FOREIGN PATENT DOCUMENTS 2116549  9/1983  United Kingdom ............... 435/138

OTHER PUBLICATIONS

Fundamentals of Enzymology, 1982, pp. 15–43.
Chemical Abstracts, vol. 67, No. 23, dated Dec. 24, 1967, p. 9924, Abstract No. 105462P, entitled "5-Ketogluconic Acid Reductase", 1979.
2340 Agricultural and Biological Chemistry, vol. 43, No. 1, "Crystallization and Properties of 5-Keto-D-gluconate Reductase from Gluconobacter suboxydans.
"Production of 2-Keto-L-Gulonate, an Intermediate in L-Ascorbate Synthesis, by a Genetically Modified Erwinia herbicola by S. Anderson, et al., in Science, vol. 230, Oct. 1985, pp. 144–149.

*Primary Examiner*—Lionel M. Shapiro
*Attorney, Agent, or Firm*—Birch, Stewart, Kolasch & Birch

[57] ABSTRACT

A novel reductase is produced from a microorganism which belongs to genus Corynebacterium and is useful as a catalyst which catalyzes, in the presence of NADPH, reduction of 2, 5-diketo-D-gluconic acid or its salts to 2-keto-L-gulonate or the corresponding salts thereof. It also catalyzes reduction of 5-keto-D-fructose to sorbose, in the presence of NADPH.

23 Claims, No Drawings

2,5-DIKETO-D-GLUCONIC ACID REDUCTASE

BACKGROUND AND FIELD OF THE INVENTION

The present invention relates to 2,5-diketo-D-gluconic acid reductase (hereinafter, abbreviated to as 25DKG-Rase) and its production.

The disclosed enzyme has an action of catalyzing, in the presence of reduced nicotinamide adenine dinucleotide phosphate (abbreviated to as NADPH), reduction of 2,5-diketo-D-gluconic acid (abbreviated to as 25DKG) to 2-keto-L-gulonic acid (abbreviated to as 2KLG), the precursor of vitamin C. It also has an action of catalyzing reduction of 5-keto-D-fructose (abbreviated to as 5KF) to L-sorbose.

DESCRIPTION OF THE PRIOR ART

2KLG production from 25DKG by the use of cell extract obtained from a microorganism which belongs to genus Corynebacterium has been disclosed in, for instance, European Patent Publication No. 00 88 408 and UK Patent Publication No. 2 116 549. However, no disclosure had ever been given on a purified enzyme which holds both of the stated enzyme actions compatibly and requires NADPH in common in demonstrating the either action.

SUMMARY OF THE INVENTION

It is therefore the object of the present invention to provide the novel 25DKG-Rase.

It is another object to provide a process of producing the novel 25DKG-Rase.

According to the present invention, there is provided a 25DKG-Rase having the following physico-chemical properties:
(a) enzyme action; catalyzes, in the presence of NADPH as a coenzyme,
  (i) reduction of 25DKG or its salts to 2KLG or the corresponding salts thereof and
  (ii) reduction of 5KF to L-sorbose.
(b) specificities for substrates; shows specificities for 25DKG and 5KF.
(c) optimum pH: pH 6-7
(d) pH stability: pH 5-7
(e) molecular weight: 29, 000±2, 000
(f) isoelectric point: pH 4.4±0.3

In another aspect of the present invention, there is provided a process for producing this novel enzyme by isolating it from disrupted cells of a microorganism which belongs to genus Corynebacterium.

In the course of study on enzymes which reduce 25DKG carried by a number of 2KLG-producing microorganisms, the present inventors have found that a 25DKG-Rase obtained from 2KLG-producing strains which belong to genus Corynebacterium has the catalytic action, in the presence of NADPH, of (i)reducing 25DKG to 2KLG, and (ii)reducing 5KF to L-sorbose. And they have completed the present invention by succeeding in isolating and purifying the novel enzyme which has previously undisclosed actions. For instance, the compatible holding of both actions is a particularly unprecedented discovery.

Although the enzyme has the enzyme actions on 25DKG and 5KF, it does not reduce 5-keto-D-gluconic acid which shares the presence of keto-group at 5th position that is common to these two substrates. In addition, it does not show reducing action either on ketose such as D-fructose and L-sorbose having keto-group adjacent to the terminal alcoholic hydroxy group, or on 2KLG or 2-keto-D-gluconic acid.

The enzyme is an intracellular enzyme extracted from the cells of the 2KLG producing strain belonging to genus Corynebacterium. As the microorganisms useful in the process of the present invention, there is exemplified Corynebacterium sp. No. 20A-77, ATCC 31,090, FERM-P 2,770, one of the 2KLG producing strain belonging to genus Corynebacterium, and a mutant derived from this strain (for instance, a mutant defective in metabolizing 5-keto-D-gluconic acid, FERM-BP 108). In addition, Corynebacterium sp. No. T13, ATCC 31,089, Corynebacterium sp. No. K-106, ATCC 31,088, and any mutant derived from these strain may also be used as the source of the enzyme.

These microorganisms are deposited with the Fermentation Research Institute, Yatabe, Japan as FERM-Ps or FERM-BPs and/or with the American Type Culture Collection, Maryland, U.S.A. as ATCCs by the present inventors, and samples of these are available from those depositories under the provision of the Budapest Treaty.

Detailed Taxonomical descriptions of the strains No. 20A-77, T-13 and K-106 are given in, for instance, U.S. Pat. No. 3,959,076 and the method of inductive mutation to FERM-BP 108 strain from the parent 20A-77 strain is disclosed in detail in, for instance, European Patent Publication No. 0088,408.

No particular restriction should be imposed on the composition of the nutrient medium used for the the growth of the 2KLG-producing strains to produce 25KG-Rase of the present invention. The medium should desirably contain carbon sources, nitrogen sources, other inorganic salts, and trace amounts of other factors which are assimilable by the strains. As the carbon source, sugars such as D-glucose and sucrose, organic acid such as gluconic acid, glycerol and the like may be used in an aqueous medium at 1-3%. As the nitrogen source, polypeptone, corn steep liquor and the like may be used at 0.5-5%. Phosphate, magnesium salt, vitamin and trace amount of other metal salts essential for the growth may also be used. The medium is inoculated with the previously described 2KLG-producing strain and then is cultured at 25°-35° C. for 15-30 hours for the growth of the strain.

As the method for extracting the intracellular enzyme from the broth after the growth, the following ones can be exemplified. Namely, cells are first harvested from the broth by centrifuge and washed with water, physiological saline or a buffer solution of an appropriate pH. The washed cells are suspended in a buffer of an appropriate pH and are disrupted by means of sonication, a french press or a treatment with an enzyme (lysozyme). Removal of unbroken cells and cell debris from the disrupted solution by centrifuge or the like will give a supernatant (crude enzyme solution). Ammonium sulfate is added to the crude enzyme solution to salt out (30-70% saturated fraction).

The salted-out product is dissolved in a buffer appropriately prepared so that the enzyme may not be inactivated and the solution is subjected to dialysis to remove the remainining ammonium sulphate. Thereafter, the enzyme solution is subjected to (a) purification treatment(s) such as ion-exchange chromatography and affinity chromatography to give the purified 25DKG-Rase, as single component.

The physico-chemical properties of the purified 25DKG-Rase can be illucidated together with their measurements as follows:

(1) Action:

25DKG+NADPH+H$^+$→2KLG+NADP$^+$

5KF+NADPH+H$^+$→L-sorbose+NADP$^+$

As shown, NADPH is used as a hydrogen donor in the above reaction. Reduced nicotinamide adenine dinucleotide (NADH) may also be used as the hydrogen donor in the above reaction but the reaction velocity in that case is lowered to one two hundred and fiftieth (1/250) or less of that in the reaction where NADPH is used.

(2) Specificities for substrates:

The enzyme shows specificities for 25DKG and 5KF. It however does not reduce 5-keto-D-gluconic acid which shares a similarity with the two substrates and does not show any reducing action on ketoses having a keto-group adjacent to the terminal alcoholic hydroxy group such as D-fructose and L-sorbose and on such compounds having a keto-group at the 2-position such as 2KLG and 2-keto-D-gluconic acid.

No or not substantial production of 25DKG or 5KF from 2KLG or L-sorbose is recognized in the presence of NADP or NAD.

(3) Optimum pH: pH 6-7

(4) PH stability: pH 5-7

(determined on the basis of residual activities after treatments in 0.1M dimethylglutaric acid buffer for pH 4-5, in 0.1M Good buffer (PIPES) for pH 6-7 and in 0.1M Tris-HCl buffer for ph 8-9 at 28° C. for 30 minutes). Residual activity of 70% or more is recognized in pH 5-7 while only those of 30% or less are recognized in pH 4 or below, and in pH 8 or above.

(5) Measurement of enzymatic activity:

The enzymatic activity is spectrophotometrically measured on the basis of the decrease in absorption at 340 nm which corresponds to the oxidation of NADPH as the result of the enzyme reaction at 30° C. in 0.1M Tris buffer (pH 7) containing 0.1 mM NADPH and 3.3 mM Ca-25DKG. One unit of the enzymatic activity is defined as that oxidizes 1 μmole of NADPH for one minute.

(6) Range of reaction temperature; 25°-45° C.

(7) Inactivation conditions of pH and temperature:

Ninety-six (96) % or more of the activity is lost after being stood at pH 4 or below, or pH 8 or above and at 28° C. for 2 hours.

(8) Inhibition, activation and stabilization:

The enzyme is inhibited by oxalate and scarcely inhibited by glyceroaldehyde. No remarkable increase in activation is observed by the addition of Mg$^{++}$ or Mn$^{++}$. It is stabilized by glycerol of a high concentration (30-50%) or sucrose (1M).

(9) Molecular weight: 29,000±2,000 (measured by SDS-polyacrylamide electrophoresis and gel filtration).

(10) Isoelectric point: pH 4.4±0.3 (measured by isoelectric point electrophoresis).

(11) Km value: 2.2±1.5 mM (25DKG substrate in 0.1M Tris buffer (pH 7.0) at 30° C.)

The 25DKG-Rase of the present invention is available for the uses where the above described enzyme action is demonstrated. Namely, 2KLG and L-sorbose can be produced from 25DKG and 5-keto-fructose, respectively, in the presence of the coenzyme, NADPH. In the case of 2KLG production, for instance, the reaction usually proceeds at 25°-45° C. and pH 6-7. The molar concentration of the substrate, 25DKG which participates in the reaction is equal to that of the hydrogen donor, NADPH and should be determined in accordance with the common knowledge relating to enzyme reaction. However, that in the range of 20-200 mM is considered to be appropriate.

The enzyme may preferably be allowed to react with the substrate in a concentration ranging from 0.5 to 5.0 unit/ml. In the reaction, the enzyme may also be used in an immobilized state with an appropriate carrier. Any means of immobilization generally known to the art of enzyme may be used. For instance, the enzyme may be bound directly to a membrane, granules or the like of a resin having (a) functional group(s), or it may be bound through bridging compounds having (a) bifunctional group(s), for example, glutaraldehyde, to the resin.

The time of said enzyme reaction should not particularly be limited though, 90% or more of 25DKG of the substrate can be reduced to 2KLG in the reaction performed at 30° C. for 60-120 minutes.

DESCRIPTION OF THE PREFERRED EMBODIMENTS

In the followings, the present invention will be described in more detail by way of example.

EXAMPLE 1

(1) Culture of cells (i) Seed medium

A medium (60 ml) of the following composition was placed in a 500 ml flask and sterilized at 120° C. for 15 minutes:

| | |
|---|---|
| D-glucose | 1.0% |
| Yeast extract (Difco) | 0.5% |
| Bacto-peptone (Difco) | 0.5% |
| NaNO$_3$ | 0.1% |
| KH$_2$PO$_4$ | 0.1% |
| MgSO$_4$.7H$_2$O | 0.02% |
| pH 7.0 | |

(ii) Medium for growth

A medium (20 L) of the following composition with 50 ppm of an antifoam (polypropylene glycol P-2000) was placed in a 30 L jar fermenter and sterilized at 120° C. for 20 minutes:

| | |
|---|---|
| D-glucose | 2.0% |
| Corn steep liquor | 3.0% |
| Yeast extract | 0.1% |
| NaNO$_3$ | 0.3% |
| KH$_2$PO$_4$ | 0.06% |
| pH 7.2 | |

(iii) Culture

Each of ten (10) seed media was inoculated with each one loopful of the mutant (FERM-BP 108) derived from Corynebacterium sp. No. 20A-77 and incubated in a rotary shaker (amplitude, 71 mm, 270 r.p.m.) at 28° C. for 18 hours. The incubated media (10) were transferred to the medium for growth which was cultured at 28° C. for 22 hours with an air flow rate of 0.5 vvm and agitation at 400 r.p.m. (OD=19).

(2) Extraction of the Enzyme

The cells in the incubated broth obtained in (1) above were collected therefrom by means of centrifuge (Sharpless centrifuge; 10,000 G for 10 min.) and washed with 0.1M tris buffer (hereinafter, abbreviated to as TB and being adjusted to pH 7.0 if not otherwise specified). The washed cells were suspended in 0.1M TB so that the OD of the suspension was made 150 and disrupted by means of sonication (160 watt/80 ml. for 7 min.). Unbroken cells and cell debris were removed from the sonicated solution by centrifuge (15,000 G for 30 min.) to give about 1 L of supernatant (protein=10.3 mg/ml, 25DKG-Rase=0.63 unit/ml).

(3) Purification of the Enzyme (All of the following procedures were performed at 4° C. or below)

(i) Fractionation with ammonium sulfate

Ammonium sulfate was added to the supernatant obtained above (2) to 30% saturation and the salted-out product was removed by centrifuge (10,000 G for 10 min.). To the thus obtained supernatant, ammonium sulfate was added to 70% saturation. After being cooled with ice for about 1 hour, the precipitated protein was collected by centrifuge (10,000 G for 10 min.). The protein was dissolved in 200 ml of 0.1 M TB and the solution was dialyzed against 0.02M TB overnight.

(ii) Ion-exchanging chromatography

The dialyzed solution (250 ml, protein; 13.6 mg/ml) obtained above (i) was applied to a DEAE-sephalose CL-6B column (available from Pharmacia Finechemicals Co.) and subjected to chromatography under the following conditions:

Column size: 1.6×30 cm, Equilibrating liquid: 0.02M TB, Eluent=0.02M TB (200 ml) - - - - - - 0.15M NaCl/0.02M TB (300 ml) - - - - - - 0.25M NaCl/0.02M TB (200 ml)

The eluate was divided into 5 ml fractions and enzymatic activities of the respective fractions for substrates of Ca-25DKG and 5KF were measured for each fractions in a manner which will be described later in (5)-(ii). As the results, the enzymatic activities for both substrates were observed in 80 ml of eluate eluted with 0.25M NaCl/0.02M TB.

Then, ammonium sulfate was added to the eluate to 70% saturation to salt the protein out and the salted-out product was dissolved in 30 ml of 0.1M TB and dialyzed against 0.02M TB at 4° C. overnight.

(iii) Affinity chromatography

The dialyzed solution obtained above (3)-(ii) was applied to a Amicon Matrix Gel Red A column (available from Amicon Far East Limited) which had previously been equilibrated with 0.02M TB and subjected to chromatography under the following conditions:

Column size: 1.6×19 cm, Washing liquid: 0.4M NaCl/0.02M TB (400 ml), Eluent=0.5M NaCl/0.02M TB (450 ml) - - - - - 0.7M NaCl/0.02M TB (150 ml) - - - - - 1M NaCl/0.02M TB (300 ml).

As the results of enzymatic activity meansurements of the respective fractions (each 5 ml) in the same manner as (3)-(ii), the enzymatic activities for the both substrates of 25DKG and 5KF were observed in the eluates of 18 fractions eluted with 0.7M-1.0M NaCl/0.02M TB. Two hundred twenty-five (225) ml of 0.02M TB was added to the collected active fractions (90 ml) to lower the solution's NaCl concentration and the mixture was applied again to an Amicon Matrix Gel Red A Column (1.9×13 cm). The column was washed with 120 ml of 0.2M NaCl/0.02M TB and eluted with 150 ml of 0.02M TB containing 0.5 mM NADPH and 0.2M NaCl. The eluate was portioned to 5 ml fractions whose enzymatic activities were measured as described above. As the results, it was found that the fractions (about 35 ml) having high enzymatic activity were obtained in those (about 70 ml) eluted with 0.02M TB containing 0.5 mM NADPH and 0.2M NaCl.

(iv) Concentration of enzyme and removal of NADPH

To the eluate obtained above (iii), ammonium sulfate was added to 30% saturation and applied to a Phenyl sephalose CL-4B column (0.9×3 cm, available from Pharmacia Finechemicals Co.) which had previously been equilibriated with 0.02M TB containing ammonium sulfate in 30% saturation. The column was washed with 0.02M TB containing ammonium sulfate of 30% saturation to completely remove NADPH whose removal was confirmed by the measurement of absorption at 340 nm and the enzyme in the column was eluted with 0.02M TB which was then portioned to 1 ml fractions.

As the results of the enzymatic activity measurements of these fractions, high activity is observed with four (4) fractions. The four fractions collected to define as a purified enzyme solution were used in the subsequent measurements. This solution showed a 54 units/ml. 25DKG-Rase activity and contained 0.58 mg/ml protein.

(4) Purity of the purified enzyme solution

Two to five (2-5) μl of the purified enzyme solution obtained above (3) was analyzed by means of SDS-polyacrylamide gel electrophoresis (separating gel; 10% acrylamide, conditions of phoresis; 40 mA at room temperature for 1 hr.) wherein the enzyme was focused to single band at a position which corresponds to that of molecular weight 29,000±2,000.

As the results of further analyses by means of gel filtration (Sephadex G-100), an enzymatic activity was observed in the fractions which corresponds to those of molecular weight 29,000±2,000.

Five (5) μl of the enzyme solution was then subjected to isoelectric point electrophoresis (gel; polyacrylamide: conditions of phoresis(a); pH interval 2.5-5; anode electrolyte=0.1M $H_2SO_4$ cathode electrolyte=0.1M NaOH, 6W, 2,700 VH: conditions of phoresis(b); pH interval 4.0-6.5; anode electrolyte=0.04M DL-glutamic acid, cathode electrolyte=0.2M NaOH, 25W, 2,600 VH; temperature, 18°-20° C.) to give a result that the enzyme migrated in a single band at a position which corresponds to pH 4.4±0.2. From the previously-described facts, it was confirmed that the purified enzyme solution was one which solely contains 25DKG-Rase.

(5) Measurements of Physico-chemical properties (i) Enzyme reaction

The purified enzyme solution (10 μl) obtained above (3) was mixed with 25 μmoles of a substrate (Ca-25DKG or 5KF) and 3.0 ml of 0.01M TB (pH 7) containing 15 μmoles of NADPH and the mixture was allowed to react at 30° C. for 60 minutes. After the reaction, the reaction mixture was analyzed by paper chromatography (developing solvent; phenol:formic acid:water=75:4:25, chromogenic agent; AHF solution, prepared by dissolving 0.93 g of anilin and 1.66 g of phthalic acid in 100 ml of water-saturated n-butanol and heating at 105° C. for 2 minutes) and by gas chromatography (column; SE-52, carrier gas: Helium, sample; trimethylsilylated derivative). As the results of the analysis in both chromatographies, it was found that only 2KLG is produced from 25DKG and only L-sorbose is produced from 5KF. In Table 1, the results of quantitative determination of the products by gas chromatography are shown.

TABLE 1

| Reduction of 25DKG and 5KF by purified enzyme solution | | |
|---|---|---|
| Substrate | Product | Concentration of the product |
| Ca-25DKG | Ca-2KLG | 845 μg/ml |
| 5KF | L-sorbose | 795 μg/ml |

(ii) Substrate specificity

Two point nine (2.9) ml of 0.1M TB (pH 7) containing 0.3 μmoles of NADPH was placed in a quartz cubette having 1 cm optical length difference and added 1-5 μl of the enzyme solution obtained above (3) thereto. Then, to the mixture, each 0.1 ml of the various substrate solutions (0.1M) were added while being kept at 30° C. Reactivities of the enzyme on the respective substrates were determined, by means of successive measurement of the decrease in absorption at 340 nm, on the basis of the decrease for 1 minute. The results of the measurement are shown in Table 2 which follows;

TABLE 2

| Specificity of 25DKG-Rase for various substrates | |
|---|---|
| Substrate | Activity of the purified enzyme solution (1 ml) |
| Ca-25DKG | 54 units |
| 5KF | 94 units |
| K-5-keto-gluconate | 0 units |
| D-fructose | 0 units |
| L-sorbose | 0 units |
| Ca-2-keto-D-gluconate | 0 units |
| Na-2KLG | 0 units |

As evident from the above table, it is confirmed that the enzyme of the present invention shows a high activity for 25DKG or 5KF but does not show any reductive activity for 5-keto-D-gluconic acid, D-fructose, L-sorbose, 2-keto-D-gluconic acid and 2KLG.

(iii) On coenzyme (hydrogen donor)

NADH was substituted for the NADPH in the reaction system of (5)-(ii) and the enzymatic activities of the 25DKG-Rase for substrates, Ca-25DKG and 5KF were measured. The results of the measurements are shown in Table 3 which follows.

TABLE 3

| The effect of coenzymes on 25DKG-Rase activity | | |
|---|---|---|
| | Enzymatic activity (unit/1 ml of the purified enzyme solution) Coenzyme: | |
| Substrate | NADPH | NADH |
| Ca-25DKG | 54 | 0.2> |
| 5KF | 94 | 0.2> |

As shown in the above table, the enzyme of the present invention showed enzymatic activity of 54 units/1 ml of the purified enzyme solution on Ca-25DKG when the enzyme is used together with NADPH whereas it showed that of only 0.2 unit or less if combined with NADH. Likewise, the activity of 94 units on 5KF with NADPH decreased to 0.2 unit or less with NADH.

(iv) Optimum pH

In order to clarify the relation between the reaction velocity of the 25DKG-Rase and pH, the enzymatic activities were measured by using the following buffers in place of the buffer of the reaction system in (5)-(ii).

pH 4.0–5.0: 0.1M 3,3-dimethylglutaric acid buffer.

pH 6.0–7.0: 0.1M Good buffer (PIPES: piperazine-N,N-bis-(2-ethane) sulfonic acid)

pH 7.0–9.0: 0.1M Tris buffer.

The results of the measurements of the enzymatic activities on the substrates, Ca-25DKG and 5KF at the respective pHs are shown in Table 4 below.

TABLE 4

| 25DKG-Rase activity on pH in the enzyme reaction | | | |
|---|---|---|---|
| | | Enzymatic activity[a]:(unit/ml) Substrate | |
| pH | Buffer | Ca-25DKG | 5KF |
| 4.0 | 3,3-dimethyl-glutaric acid | 1 | 2 |
| 5.0 | 3,3-dimethyl-glutaric acid | 22 | 33 |
| 6.0 | Good (PIPES) | 59 | 96 |
| 6.5 | Good (PIPES) | 57 | 95 |
| 7.0 | Good (PIPES) | 53 | 92 |
| 7.0 | Tris | 54 | 93 |
| 7.5 | Tris | 44 | 68 |
| 8.0 | Tris | 32 | 48 |
| 8.5 | Tris | 11 | 27 |
| 9.0 | Tris | 7 | 13 |

[a]Enzymatic activity of units per 1 ml of the purified enzyme solution.

As evident from the above table, the enzyme showed the highest enzymatic activity at pH 6-7.

(v) Temperature for action

The reaction velocities in the reaction system of (5)-(ii) which employs the substrate, Ca-25DKG were measured at varying temperatures from 15° to 50° C. The results thereof are shown in Table 5 below.

TABLE 5

| 25DKG-Rase activity on temperature | |
|---|---|
| Temperature °C. | Enzymatic activity (unit/ml) |
| 15 | 14 |
| 25 | 29 |
| 27.5 | 44 |
| 30 | 54 |
| 32.5 | 59 |
| 35 | 64 |
| 40 | 67 |
| 45 | 44 |
| 50 | 10 |

Enzymatic activity: per 1 ml of the purified enzyme solution on the substrate, Ca-25DKG at pH 7.

As evident from the above table, it is confirmed that the enzyme of the present invention increases its enzymatic activity with the rise in temperature up to 40° C. but the activity decreases with the rise in temperature at 45° C. or above.

(vi) Measurement of Km value

In the procedure described in (5)-(ii) above, the velocities of reducing reactions in varying concentrations of Ca-25DKG from 0.01M to 0.25M were measured, respectively, to determine the Km value for 25DKG. As the results, the Km value was found to be 1.8±1.0 mM.

EXAMPLE 2

(1) Culture of cells (i) Medium for growth

A medium (12 L) of the following composition is placed in a 20 L jar fermenter and sterilized at 120° C. for 20 minutes:

| D-glucose | 1.0% |
|---|---|
| Corn steep Liquor | 1.0% |

| -continued | |
|---|---|
| Yeast extract (Difco) | 0.2% |
| Polypeptone (Difco) | 0.5% |
| KH$_2$PO$_4$ | 0.1% |
| MgSO$_4$.7H$_2$O | 0.02% |
| pH 7 | |

(ii) Culture

Two seed cultures for each of Corynebacterium sp. No. K-106 (ATCC 31,088, abbreviated to as K-106) and Corynebacterium sp. No. T-13 (ATCC 31,089, abbreviated to as T-13) were prepared with the medium and in the procedures described in Example 1 (1).

Each of these seed cultures was inoculated in each of the media prepared in (i) above and cultured at 28° C. for 18 hours with aeration of 0.5 vvm and agitation at 400 r.p.m.. The amount of cells represented by OD at the end of the culture were as follows: OD=11.8 for Strain No. K-106; OD=12.2 for No. T-13.

(2) Extraction of enzyme

Cell suspensions of OD=150 in 0.02M TB of Strains Nos. K-106 and T-13 were prepared by washing the cells from the cultured broths in accordance with the method described in Example 1-(2). The cells in the suspensions were disrupted by means of French press (700 kg/cm$^2$). The disrupted solutions were subjected to centrifuge (15,000 G, 30 min.) as described in Example 1-(2) to remove unbroken cells and cell debris. As the results, cell extracts having the following enzymatic activities were obtained.

| Strain | Amount of extract | Protein | 25DKG-Rase activity |
|---|---|---|---|
| K-106 | 400 ml | 10 mg/ml | 2.1 units/ml |
| T-13 | 400 ml | 12 mg/ml | 2.0 units/ml |

(3) Purification of enzyme (i) Salting-out with ammonium sulfate

Proteins corresponding to the fractions salted out with ammonium sulfate of 30–70% saturation were collected in the same method as described in Example 1-(3) and dissolved in 0.02M TB which solutions were dialyzed against 0.02M TB at 4° C. overnight.

As the results, the dialyzed solutions having the following enzymatic activities were obtained;

| Strain | Amount of enzyme solution | Protein | 25DKG-Rase activity |
|---|---|---|---|
| K-106 | 74 ml | (Not tested) | 7.0 units/ml |
| T-13 | 88 ml | 11.1 mg/ml | 4.8 units/ml |

(ii) Ion-exchanging chromatography

The method described in Example 1-(3)-(ii) was applied to the enzyme solutions. As the results, the eluants having the following enzymatic activities were obtained.

| Strain | Amount of enzyme solution | Protein | 25DKG-Rase activity |
|---|---|---|---|
| K-106 | 49 ml | 0.60 mg/ml | 2.4 units/ml |
| T-13 | 52 ml | 0.94 mg/ml | 4.1 units/ml |

(iii) Affinity chromatography

Ammonium sulfate was added to each of the eluants obtained in (ii) above to 30% saturation, and the enzymes therein were concentrated and desalted by means of Phenyl sephalose gel column chromatography in accordance with the method described in Example 1-(3)-(iv). The concentrated enzyme solutions were purified twice by affinity chromatography with Amicon Matrix Gel Red A Column, as described in Example 1-(3)-(iii). As the results, the 25DKG-Rases derived from the both strains were in the fractions eluted with the eluent of 0.7-1M NaCl concentration in the first chromatography and in the fractions with 0.5 mM NADPH in the second chromatography.

The eluants were desalted and concentrated after the NADPH removal by the method described in Example 1-(3)-(iv).

As a result, the purified enzyme solutions having the following activities were obtained:

| Strain | Amount of enzyme solution | Protein | 25DKG-Rase activity |
|---|---|---|---|
| K-106 | Ca 1 ml | 0.25 mg/ml | 23.8 units/ml |
| T-13 | Ca 2 ml | 0.17 mg/ml | 15.1 units/ml |

The above enzyme solutions (2–10 μl) were assayed by means of SDS-polyacrylamide gel electrophoresis and isoelectric electrophoresis described in Example 1-(4) wherein either one of the enzymes showed a single band. The purified enzyme solutions were subjected to the following meansurement of the properties.

(4) Physico-chemical properties of the enzymes

The measurements of the physico-chemical properties were conducted in a manner as described in Example 1-(4)---(5).

(i) Molecular weight

As the results of assays according to SDS-polyacrylamide gel electrophoresis, the molecular weights of both of the 25DKG-Rases derived from Strain K-106 and T-13 were found to be 29,000±2,000.

(ii) Isoelectric point

The results of the isoelectric point electrophoreses for the enzymes derived from Strains K-106 and T-13 were pH 4.4±0.2 and pH 4.5±0.2, respectively.

(iii) Substrate specificity

Either one of the enzymes produced only Ca-2KLG from Ca-25DKG and only L-sorbose from 5KF. None was produced from 5-keto-D-gluconic acid, D-fructose, L-sorbose, 2KLG and 2-keto-D-gluconic acid.

(iv) Enzymatic activity

The enzyme from Strain K-106 had activity for Ca-25DKG of 23.8 units/ml (95 units/mg protein) and that for 5KF of 38.3 units/ml (152 units/mg protein). While, the enzyme from Strain T-13 had activity for Ca-25DKG of 15.1 units/ml (89 units/mg protein) and that for 5KF of 39 units/ml (229 units/mg protein).

(v) Coenzyme (hydrogen donor)

The results of measurement on the enzymatic activity of the both enzyme for Ca-25DKG using NADH as the coenzyme gave the activity of 0.1 unit/ml or less in either case.

(vi) Optimum pH

Enzymatic activities of 25DKG-Rases obtained from K-106 and T-13 were measured at varying pH from 4 to 9 (substrate: Ca-25DKG, reaction temperature: 30° C.). The results thereof were shown in Table 6 below.

TABLE 6

Enzymatic activities of 25DKG-Rases obtained from K-106 and T-13 on pH of the enzyme reaction

| pH | Enzymatic activity (relative activity)* | |
|---|---|---|
| | k-106 | T-13 |
| 4.0 | 1 | 1 |
| 5.0 | 48 | 65 |
| 6.0 | 103 | 104 |
| 7.0 | 100 | 100 |
| 8.0 | 70 | 64 |
| 9.0 | 6 | 19 |

*Activity at each pH defined on the basis that equals 100 at pH 7, 30° C.

As evident from the above table, it is confirmed that optimum pH of either of 25DKG-Rases obtained from the both strains is pH 6-7.

(vii) Temperature for action

The enzymatic activities of 25DKG-Rases obtained from K-106 and T-13 were measured at varying temperature (pH 7.0, substrate: Ca-25DKG). The results thereof were shown in Table 7 below.

TABLE 7

Enzymatic activity of 25DKG-Rases obtained from K-106 and T-13 on reaction temperature

| Temperature (°C.) | Enzymatic activity (relative activity*) | |
|---|---|---|
| | K-106 | T-13 |
| 22 | 46 | 64 |
| 25 | 69 | 79 |
| 28 | 86 | 92 |
| 30 | 100 | 100 |
| 35 | 115 | 115 |
| 40 | 119 | 133 |
| 45 | 93 | 128 |
| 50 | 44 | 92 |

*As defined in the former Table 6.

As evident from the above table, it is confirmed that the activities of 25DKG-Rases obtained from the both strains each increases with the rise of temperature up to 40° C. but decreases with the rise of temperature above 45° C.

(viii) Km value

Km values of the both enzymes on 25DKG measured by using purified enzyme solutions of K-106 and T-13 were 1.7±1.0 mM and 2.6±1.0 mM, respectively.

What is claimed is:

1. Substantially pure 2,5-Diketo-D-gluconic acid reductase having the following physio-chemical properties:
   (a) enzyme action: catalyzes, in the presence of NADPH as a coenzyme,
      (i) reduction of 2,5-diketo-D-gluconic acid or its salts to 2-keto-L-gulonic acid or the corresponding salts thereof, and
      (ii) reduction of 5-keto-D-fructose to L-sorbose;
   (b) substrate specificity to: 2,5-diketo-D-gluconic acid and 5-keto-D-fructose;
   (c) optimum pH: pH 6-7;
   (d) pH stability: pH 5-7;
   (e) molecular weight: 29,000±2,000; and
   (f) isoelectric point: pH 4.4±0.3.

2. A process for the production of 2,5-diketo-D-gluconic acid reductase, which comprises:
   culturing a microorganism belonging to the genus Corynebacterium in a nutrient medium containing carbon and nitrogen sources and inorganic salt, and isolating the thus produced 2,5-diketo-D-gluconic acid reductase from disrupted cells of the microorganism as a single component which can reduce 5-keto-D-fructose to L-sorbose.

3. A composition of matter comprising 2,5-Diketo-D-gluconic acid reductase as a single component which exhibits the following physio-chemical properties:
   (a) enzyme: action: catalyzes, in the presence of NADPH as a coenzyme,
      (i) reduction of 2,5-diketo-D-gluconic acid or its salts to 2-keto-L-gulonic acid or the corresponding salts thereof, and
      (ii) reduction of 5-D-fructose to L-sorbose;
   (b) substrate specificity to: 2,5-diketo-D-gluconic acid and 5-keto-D-fructose;
   (c) an optimum pH of from 6 to 7;
   (d) a pH stability of from 5 to 7;
   (e) a molecular weight of 29,000±2,000; and
   (f) an isoelectric point at a pH of 4.4±0.3.

4. A process for converting 2,5-diketo-D-gluconic acid into 2-keto-L-gulonic acid comprising contacting 2,5-diketo-D-gluconic acid with an effective amount of the enzyme composition of claim 3.

5. A process for converting 5-keto-D-fructose into L-sorbose which comprises contacting 5-keto-D-fructose with a purified 2,5-Diketo-D-gluconic acid reductase enzyme composition which exhibits the following physio-chemical properties:
   (a) enzyme: action: catalyzes, in the presence of NADPH as a coenzyme,
      (i) reduction of 2,5-diketo-D-gluconic acid or its salts to 2-keto-L-gulonic acid or the corresponding salts thereof, and
      (ii) reduction of 5-D-fructose to L-sorbose;
   (b) substrate specificity to: 2,5-diketo-D-gluconic acid and 5-keto-D-fructose;
   (c) an optimum pH of from 6 to 7;
   (d) a pH stability of from 5 to 7;
   (e) a molecular weight of 29,000±2,000; and
   (f) an isoelectric point at a pH of 4.4±0.3.

6. The composition of matter according to claim 3, wherein the enzyme is an intracellular enzyme extracted from a microorganism belonging to the genus Corynebacterium.

7. The composition of matter according to claim 6, wherein the Corynebacterium microorganism is selected from the group consisting of ATCC 31,090; FERM-BP 108; ATCC 31,098; ATCC 31,088 and any mutant derived therefrom.

8. The composition according to claim 3, wherein said enzyme is catalytically active at temperatures ranging from 25° to 45° C.

9. The composition according to claim 3 further comprising a stabilizer selected from the group consisting of glycerol and sucrose.

10. The process according to claim 2, wherein the culturing is at 25°-35° C. for 15-30 hours during microbial growth.

11. A process for the production of 2,5-diketo-D-gluconic acid reductase, which comprises:
   culturing a microorganism belonging to genus Corynebacterium in a nutrient medium containing carbon and nitrogen sources and inorganic salt during the growth phase of said microorganism;
   harvesting the microorganism by centrifugation;
   disrupting the harvested cells by sonification, french press treatment or enzyme treatment;
   separating unbroken cells and cell debris from a supernatant enzyme solution;

salting-out crude enzyme solution from the supernatant enzyme solution with a salting-out solution;

dissolving the salted-out crude enzyme solution in a buffer so that the enzyme is not inactivated;

dialyzing the enzyme solution to remove the salting-out solution; and purifying the enzyme solution by ion-exhange chromatography and affinity, chromatography to produce purified 2,5-diketo-D-gluconic acid reductase as a single component.

12. The process according to claim 4, wherein the contacting occurs at 24°–45° C. and pH 6–7.

13. The process according to claim 4, wherein the molar concentration of 2,5-diketo-D-gluconic acid is equal to that of the coenzyme.

14. The process according to claim 13, wherein the molar concentration of said 2,5-diketo-D-gluconic acid is in a concentration of 20 to 200 mM.

15. The process according to claim 5, wherein the enzyme reacts with the 5-keto-D-fructose in a concentration ranging from 0.5 to 5.0 units/ml.

16. The process according to claim 5, wherein the enzyme is immobilized onto a carrier.

17. The process according to claim 4, wherein at least 90% of 2,5-diketo-D-gluconic acid is reduced to 2-keto-L-gulonic acid in 60 to 120 minutes at 30° C.

18. The process according to claim 11, wherein the salting out solution is ammonium sulfate.

19. The composition according to claim 3, wherein the Km value is 1.8±1.0 mM.

20. The enzyme composition according to claim 3 having an enzyme activity for 2,5-diketo-D-gluconic acid between 22 and 59 unit/ml and an enzyme activity for 5-keto-L-fructose between 33 and 96 unit/ml at a pH ranging from 5 to 7.

21. A composition of matter comprising 2,5-diketo-D-gluconic acid reductase as a single component which exhibits the following physio-chemical properties:

(a) enzyme catalyzing action, in the presence of a hydrogen donor as a coenzyme,
  (i) reduction of 2,5-diketo-D-gluconic acid or its salts to 2-keto-L-gulonic acid or the corresponding salts thereof, and
  (ii) reduction of 5-D-fructose to L-sorbose;
(b) substrate specificity to: 2,5-diketo-D-gluconic acid and 5-keto-D-fructose;
(c) an optimum pH of from 6 to 7;
(d) a pH stability of from 5 to 7;
(e) a molecular weight of 29,000±2,000; and
(f) an isoelectric point at a pH of 4.4±0.3.

22. A product produced by the process according to claim 11.

23. A product produced by the process according to claim 2.

* * * * *